United States Patent [19]

Welle

[11] Patent Number: 5,760,394

[45] Date of Patent: Jun. 2, 1998

[54] ISOTOPIC TAGGANT METHOD AND COMPOSITION

[76] Inventor: Richard P. Welle, 14551 Bodger Ave., Hawthorne, Calif. 90250

[21] Appl. No.: 668,648

[22] Filed: May 17, 1996

[51] Int. Cl.[6] .................................................. G01N 33/00
[52] U.S. Cl. ........................................ 250/303; 436/56
[58] Field of Search ............................ 250/303, 302, 250/260, 259; 436/27, 56

[56] References Cited

U.S. PATENT DOCUMENTS

| | | |
|---|---|---|
| 3,704,952 | 12/1972 | Bird . |
| 3,772,099 | 11/1973 | Ryan et al. . |
| 3,772,200 | 11/1973 | Livesay . |
| 3,788,814 | 1/1974 | Goldblatt et al. . |
| 3,897,284 | 7/1975 | Livesay . |
| 3,964,294 | 6/1976 | Shair et al. . |
| 4,053,433 | 10/1977 | Lee . |
| 4,131,064 | 12/1978 | Ryan et al. . |
| 4,197,104 | 4/1980 | Krystyniak et al. . |
| 4,251,726 | 2/1981 | Alvarez . |
| 4,329,393 | 5/1982 | LaPerre et al. . |
| 4,359,399 | 11/1982 | Boyars . |
| 4,363,965 | 12/1982 | Soberman et al. . |
| 4,390,452 | 6/1983 | Stevens . |
| 4,742,340 | 5/1988 | Nowik et al. . |
| 4,862,143 | 8/1989 | Hirshfeld et al. . |
| 5,057,268 | 10/1991 | Muller . |
| 5,182,051 | 1/1993 | Bandy et al. . |
| 5,474,937 | 12/1995 | Anderson et al. . |

*Primary Examiner*—Michael J. Tokar
*Assistant Examiner*—Richard Hanig
*Attorney, Agent, or Firm*—Lewis, D'Amato, Brisbois & Bisgaard LLP

[57] ABSTRACT

A system for tagging products or substances for retrospective identification using controlled abundance ratios of multiple isotopes in each of one or more elements in the tagged substance. The abundance ratios of the isotopes of the tagging elements are measured by suitable means to determine the identification code of the tagged product of substance.

24 Claims, No Drawings

ISOTOPIC TAGGANT METHOD AND COMPOSITION

BACKGROUND

There is significant interest in tagging various substances or products such as explosives, ammunition, paint, and petroleum products to provide for retrospective identification. Methods used to date generally involve the addition of materials from one or more of three categories: code-bearing microparticles, bulk chemical substances, and radioactive substances.

SUMMARY OF THE INVENTION

The present invention provides for the use of artificially controlled abundance ratios of multiple stable isotopes in each of one or more elements to form an identification code. Unique taggants, each corresponding to a unique identification code, are created by mixing unique combinations of ratios of multiple stable isotopes of one or more elements. The resulting mixture is added to the substance or product to be tagged. When identification is required, the isotope abundance ratios of the taggant element or elements are measured, and the resultant measurements are compared with the appropriate identification tagging records made at the time the substance was tagged.

DETAILED DESCRIPTION

A code based on an abundance ratio of multiple isotopes of a single element presents two distinct advantages over systems using abundance ratios of elements or compounds. First, the isotopic abundance ratios can be more precisely measured than abundance ratios of elements or compounds. Second, the isotopic abundance ratio will not be modified by non-nuclear physical or chemical processes except those specifically designed for isotope separation, so the taggant code will not be destroyed by chemical reactions or explosions.

Elements which could be used for this technique include any element with more than one stable isotope. Of the 83 non-radioactive elements known to exist on earth, 62 have more than one stable isotope, and 40 have more than two stable isotopes. The element tin (Sn) has the largest number (10) of stable isotopes for any single element. The following Table I lists the symbol of each element under the number of stable isotopes for each of the naturally occurring stable elements.

TABLE I

| Elements Grouped According to their Number of Stable Isotopes | | | | | | | | | |
|---|---|---|---|---|---|---|---|---|---|
| 1 | 2 | 3 | 4 | 5 | 6 | 7 | 8 | 9 | 10 |
| Be | H | O | S | Ti | Ca | Mo | Cd | Xe | Sn |
| F | He | Ne | Cr | Ni | Se | Ru | Te | | |
| Na | Li | Mg | Fe | Zn | Kr | Ba | | | |
| Al | B | Si | Sr | Ge | Pd | Nd | | | |
| P | C | Ar | Ce | Zr | Er | Sm | | | |
| Sc | N | K | Pb | W | Hf | Gd | | | |
| Mn | Cl | U | | Pt | | Dy | | | |
| Co | V | | | | | Yb | | | |
| As | Cu | | | | | Os | | | |
| Y | Ga | | | | | Hg | | | |
| Nb | Br | | | | | | | | |
| Rh | Rb | | | | | | | | |
| I | Ag | | | | | | | | |
| Cs | In | | | | | | | | |
| Pr | Sb | | | | | | | | |

TABLE I-continued

| Elements Grouped According to their Number of Stable Isotopes | | | | | | | | | |
|---|---|---|---|---|---|---|---|---|---|
| 1 | 2 | 3 | 4 | 5 | 6 | 7 | 8 | 9 | 10 |
| Tb | La | | | | | | | | |
| Ho | Eu | | | | | | | | |
| Tm | Lu | | | | | | | | |
| Au | Ta | | | | | | | | |
| Bi | Re | | | | | | | | |
| Th | Ir | | | | | | | | |
| | Tl | | | | | | | | |

Among the 40 elements having more than two stable isotopes, there are a total of 224 stable isotopes. These totals include some isotopes which are slightly radioactive, but which have very long half lives and are present in naturally occurring samples of the elements. In most cases, the relative concentrations of the stable isotopes found in any given element anywhere on earth are constant to within one part in fifty thousand. The abundance ratios of the isotopes present are easily and precisely measured by various techniques. Highly enriched samples of most stable isotopes are available commercially.

a. Basic System

The present invention provides for a system in which the abundance ratio of two or more isotopes in each of one or more elements in a substance is artificially controlled to provide a means for retrospective identification of the substance. For example, for labelling or tagging ten commercially prepared batches of explosives, the element europium (Eu) can be used. It has two stable isotopes with atomic masses of 151 and 153. In natural europium, these two isotopes are present in the concentrations of 47.77%, and 52.23% respectively. A code can be created for these ten batches by preparing a series of isotopic samples containing $^{151}$Eu and $^{153}$Eu in a patterned series of ten concentration ratios, such as 5/95, 15/85, 25/75, 35/65, 45/55, 55/45, 65/35, 75/25, 85/15, and 95/5, each ratio assigned to one specific batch. These samples can be prepared either with elemental europium, or with europium as an element in a compound such as $Eu_2O_3$. A small quantity of the assigned isotopic sample can be added, by any of a number of means, to the specific assigned batch of explosive to be tagged, according to the following table.

TABLE II

| Batch | $^{151}$Eu:$^{153}$Eu Abundance ratio |
|---|---|
| 0 | 5/95 |
| 1 | 15/85 |
| 2 | 25/75 |
| 3 | 35/65 |
| 4 | 45/55 |
| 5 | 55/45 |
| 6 | 65/35 |
| 7 | 75/25 |
| 8 | 85/15 |
| 9 | 95/5 |

Subsequent measurement of the concentration ratio of $^{151}$Eu to $^{153}$Eu in any of these explosive batches, or in the residue left after it explodes, would (in the absence of contamination) yield a ratio identifying the batch in which the explosive was manufactured. In this example, the ten unique values of the concentration ratio distinguish and identify each of the ten batches of explosives.

The number of possible unique codes available with the use of a single pair of isotopes depends on the precision with which the isotope concentration ratio is controlled and measured in the sample. Currently available techniques allow precisions better than 1%, so presently at least 100 unique codes can readily be constructed from a single pair of isotopes. With the advent of superior techniques, more than 100 unique codes may be constructed from each pair of isotopes.

A significant increase in the number of possible unique codes is achieved by using more than one pair of stable isotopes in creating the code. Continuing the above example, the code can be expanded by adding to the explosive an additional element (e.g. neodymium, Nd) with its own specific concentration ratio of isotopes (e.g. $^{143}$Nd and $^{146}$Nd). The code can be further expanded by adding to the explosive a third element with its specific isotope concentration ratio (e.g. dysprosium, $^{161}$Dy and $^{164}$Dy).

The following table illustrates how a system using these three pairs of isotopes can be used to create an identification code (e.g. a three digit serial number). The first column shows the serial number, and the remaining columns show the relative concentrations of the europium isotopes $^{151}$Eu and $^{153}$Eu, the neodymium isotopes $^{143}$Nd and $^{146}$Nd, and the dysprosium isotopes $^{161}$Dy and $^{163}$Dy.

TABLE III

| | Isotope Abundance Ratios | | |
|---|---|---|---|
| Serial number | $^{151}$Eu:$^{153}$Eu | $^{143}$Nd:$^{146}$Nd | $^{161}$Dy:$^{163}$Dy |
| 000 | 5/95 | 5/95 | 5/95 |
| 001 | 5/95 | 5/95 | 15/85 |
| 002 | 5/95 | 5/95 | 25/75 |
| ... | ... | ... | ... |
| 009 | 5/95 | 5/95 | 95/5 |
| 010 | 5/95 | 15/85 | 5/95 |
| 011 | 5/95 | 15/85 | 15/85 |
| ... | ... | ... | ... |
| 099 | 5/95 | 95/5 | 95/5 |
| 100 | 15/85 | 5/95 | 5/95 |
| 101 | 15/85 | 5/95 | 15/85 |
| ... | ... | ... | ... |
| 998 | 95/5 | 95/5 | 85/15 |
| 999 | 95/5 | 95/5 | 95/5 |

By reference to this table, measurement of the the three abundance ratios $^{151}$Eu:$^{153}$Eu, $^{143}$Nd:$^{146}$Nd, and $^{161}$Dy:$^{163}$Dy in a tagged substance will allow one to determine the identification code (e.g. the serial number) of the substance. In this table, not all possible entries are shown. Using the coding scheme of Table III, a total of $10^3$ or 1000 unique serial numbers can be created. Additional pairs of isotopes could be used to provide additional digits, thereby increasing the number of available serial numbers. Following the same pattern, a system using N pairs of isotopes to create serial numbers results in $10^N$ unique serial numbers.

The example illustrated in Table III utilized 10% variations in the concentration ratios of each of the isotope pairs. In fact, smaller variations in the isotopic concentration ratios can be used and measured. When two pairs of isotopes are each controlled and measured to within 1% and combined in a single code, there are $100^2$ or ten thousand (10,000) unique codes available. Three pairs of isotopes at 1% precision would provide for $100^3$ or one million (1,000,000) unique codes. By extension, N pairs of isotopes, each controlled and measured to within 1% and combined in a single code, would produce $100^N$ unique codes.

b. Background Contamination

When taggants include elements which may be found in the environment to which the tagged substance is exposed, taggant contamination may occur, possibly rendering the taggant code unreadable. For example, if a taggant using europium, which has only two stable isotopes, is contaminated with background europium, there will be a change in the isotopic abundance ratio of europium in the tagged substance. Subsequent measurement of this ratio could yield a value corresponding to an incorrect identification code. Because it is difficult to determine what fraction of the europium present in the substance derives from the environment, it is difficult to determine what europium isotope abundance ratio was present in the substance before contamination. This problem can be solved by comprising the taggant signal from multiple isotopes of an element which has at least three stable isotopes (see Table I, above), so that one or more of the stable isotopes of this element can be reserved as an indicator of background contamination.

For illustration, consider a taggant code encompassing the seven naturally occurring isotopes of neodymium. These isotopes have masses 142, 143, 144, 145, 146, 148, and 150. In naturally occurring neodymium, these isotopes have abundances of 27.16%, 12.18%, 23.83%, 8.30%, 17.17%, 5.74%, and 5.62% respectively. Selecting $^{145}$Nd as the background indicator, and the abundance ratio of $^{143}$Nd and $^{146}$Nd as the taggant code, the abundance of $^{145}$Nd would be kept at some fixed abundance measurably different from its natural abundance, while the abundances of $^{143}$Nd and $^{146}$Nd would be varied to create unique codes for each tagged substance. If a tagged substance were then contaminated by background neodymium, subsequent measurement of the neodymium abundance ratios would show an abundance of mass $^{145}$Nd different from that used in the taggant. The amount of relative change would indicate the amount of environmental neodymium contamination in the substance, so that an appropriate correction could be made to the measured abundance ratio of $^{143}$Nd and $^{146}$Nd to correctly associate the substance with its identification code.

This correction is done per the following example analysis. The information which is known and which needs to be determined is indicated by the following variables:

$\alpha$=the fraction of the recovered neodymium originating in the taggant.

$\beta$=the fraction of the recovered neodymium originating in the environment.

$A_{143}$=the measured abundance of $^{143}$Nd in the recovered sample.

$A_{145}$=the measured abundance of $^{145}$Nd in the recovered sample.

$A_{146}$=the measured abundance of $^{146}$Nd in the recovered sample.

$B_{143}$=the abundance of $^{143}$Nd in naturally occurring neodymium.

$B_{145}$=the abundance of $^{145}$Nd in naturally occurring neodymium.

$B_{146}$=the abundance of $^{146}$Nd in naturally occurring neodymium.

$T_{143}$=the abundance of $^{143}$Nd in the applied taggant.

$T_{145}$=the abundance of $^{145}$Nd in the applied taggant.

$T_{146}$=the abundance of $^{146}$Nd in the applied taggant.

Of the above variables, $A_{143}$, $A_{145}$, and $A_{146}$ are measured in the substance, $B_{143}$, $B_{145}$, and $B_{146}$ are known from the scientific literature, and $T_{145}$ would have a known value independent of the taggant code.

The taggant code is contained in the values of $T_{143}$ and $T_{146}$, which are unknown. The amount of contamination is indicated by the values of $\alpha$ and $\beta$, which are also unknown.

The measured abundances of each of the isotopes in the recovered sample are related to the abundances in the taggant and the abundances in the environment by the following relationships:

$$A_{143} = \alpha T_{143} + \beta B_{143}$$

$$A_{145} = \alpha T_{145} + \beta B_{145}$$

$$A_{146} = \alpha T_{146} + \beta B_{146}$$

and it is also known that $$\alpha + \beta = 1.000$$

Thus, there is a system with four equations and four unknowns, which can be solved using standard algebra techniques. By this method, the values of $T_{143}$ and $T_{146}$ can be calculated, and the identification code determined.

A similar process can be used with any other element having three or more naturally occurring isotopes. For an element in which N isotopes are used to encode the taggant, a similar analysis is sufficient to read the code in the presence of background contamination by solving a system of N+2 equations.

c. Application Methods

Since the taggant code signal is contained in the concentration ratios of stable isotopes, which can be significantly modified only by nuclear reactions, or by laboratory processes designed specifically for isotope separation, there is a substantial latitude in the means by which the taggant is incorporated into or attached to the products to be tagged. Many existing tagging techniques involve the use of microparticles which are marked by various methods including chemical composition, color, shape, and/or microscopic writing. Similarly, particles can be manufactured composed of the elements, or compounds or alloys of the elements, comprising this isotopic taggant. Additionally, particles can be manufactured wherein smaller particles, or compounds or alloys, containing the taggant signal are embedded in a matrix. The composition of the matrix can then be controlled to suit the requirements of the taggant application. For example, the particles could be made of magnetic or fluorescent materials to facilitate collection, of refractory materials to enhance particle survival in an explosion, or of chemically inert materials to enhance particle survival in a chemical reaction, or even of non-durable, soluble, or reactive materials to enhance taggant signal dispersal in a fluid, aerosol, or powder system. The taggants may also be incorporated into the product in forms other than as a particulate additive. For example, for an application involving paints, inks, or other liquids, the taggants could be incorporated as elements or compounds in solution with the liquid. In products manufactured in whole or in part from man-made materials such as plastics, the taggant can be incorporated in elemental or compound form either in solution or suspension in the material at the time the material is manufactured. The taggant signal will then be retained by any product made from this tagged material. Another variation involves taggants incorporated as non-volatile elements or compounds dissolved or suspended in a volatile liquid. This composition could be sprayed or otherwise applied on or in the product to be tagged. When the liquid evaporates, the residue left behind would contain the taggant signal.

d. Applications

Because of these considerations, the method of tagging using stable isotope ratios can be applied to a large variety of substances or products. In addition to those already discussed, some further applications include:

Paints

When paints are tagged, then any article coated with the paint can be identified. For example, tagging of automobile paints would allow identification of automobile parts recovered after theft. It would also allow identification of paint residues left at the scene of hit-and-run accidents. Tagging could also be used in retail spray paint cans as a simple means of allowing consumers to tag things such as home built boats, motor homes, airplanes, or other easily stolen items. In the ultimate limit, complete tagging of all retail spray paints would make it possible, when combined with an appropriate record keeping system, to trace paints used by graffiti artists.

Crude Oil or Fuel Oil

In this application, the taggant could be incorporated in solution. This would allow tracing of stolen oil, or tracing the origin of unknown oil spills. Other petroleum products such as greases and oils could be tagged in batches small enough to allow tracing of residues on auto parts, or residues left by automobiles at crime scenes.

Hazardous Wastes

Tagging of hazardous wastes at their point of origin would aid in inventory control, and allow tracing of wastes of unknown origin.

Paper and/or Ink

Tagging of paper and ink can be used to establish the authenticity of documents. A representative embodiment of this application would be serialized pens in which each pen contains uniquely tagged ink. When a document is written or signed with one of these pens, the pen would then be secured, or even destroyed, adding significant difficulty to the forgery of the document. Tagging of the paper and/or ink used in the production of currency would make accurate counterfeiting more difficult.

Gunpowder

Isotope taggants in gunpowder survive the firing of the gun, and are present in the powder residue. Samples of the residue can be obtained from the gun, the bullet, the hand of the shooter, and from other surfaces in the vicinity of the shooting. The taggant code could be read from any of these residue samples, allowing the identification code of the powder to be determined.

Tires

If the taggant is dispersed uniformly throughout the rubber making up the tire, then the taggant code could be read from any part of the tire, including the material left on roads in the form of skid marks.

Drugs

Tagging of both legal and illegal drugs has potential benefits. For legal drugs, tagging the drugs along with marking the packages would be an aid to quality control and to the tracing of tampering and illegal trade in legal drugs. Tagging of raw materials used in the manufacture of illegal drugs would aid in determining the source of drugs found on the street. This idea could be extended to include aerial spraying of taggants on crops which might be used in illegal drug manufacture. Confiscated illegal drugs could be tagged for evidentiary purposes, for tracing drugs which disappear from evidence lockers, or for use in sting operations.

Many manufactured items prone to counterfeiting or theft could benefit from tagging. Tagged threads in clothing could be used to encode information about the date, time, and place of manufacture. Tagging the bulk materials used in the manufacture of such items as compact disks, computer disks, video tapes, audio tapes, electronic circuits, and other items would be useful in tracing and prosecuting theft and counterfeiting cases involving these items.

Because the taggant code signal is carried in the isotopic composition of the elements, it will not be significantly modified by chemical reactions. This makes it possible to tag chemicals, and have the taggant code be carried in any product manufactured with those chemicals. This also allows the use of any appropriate chemical process to concentrate the elements carrying the signal to enhance its readability. This also makes it possible to use this tagging technique to aid in the verification of destruction of such items as paper documents, drugs, or counterfeit manufactured items. When most items are burned, some residue remains. An item to be destroyed would be tagged with elements known to concentrate in the residue of destruction. Since the taggant code signal is not changed by the chemical processes used for destruction, this technique can be used to establish a positive connection between the item and its residue after destruction.

e. Manufacturability

Another key feature of this invention is the ability to easily tag arbitrarily small batches of substances or products with unique tags. Microparticle taggants, however encoded, are generally manufactured in batches wherein every particle in a given batch contains the same code. Economic considerations limit the minimum size of each microparticle batch. In this invention, as illustrated above, the individual elements of the code do not have to be physically connected with one-another in order to make the code readable. The individual units of the code can be added to the substance or product to be tagged as that substance is manufactured. This can be done manually or in an automated system where each unit of the substance or product receives a different code.

For illustration, consider the tagging of small arms ammunition. In the preferred case, each individual round of ammunition would have its own unique tag. It might be economically prohibitive to produce a separate batch of microparticle taggants for each round of ammunition. With the new invention, the taggant could be introduced into the ammunition by injecting a drop of a solvent, such as ethanol, containing the taggant into the cartridge case before the propellant is introduced. The solvent would be allowed to evaporate, leaving the taggant as a dry residue on the walls of the cartridge case. The powder and bullet are then added, leaving the taggant sealed inside the cartridge case. When the cartridge is fired, some of the taggant material will be incorporated in the combustion products which propel the bullet from the gun. Some of the taggant will then further be incorporated in the residue of the combustion products which deposits on the bullet, the gun, the hand of the shooter, and other areas. The taggant code signal can then be read by measuring the isotope ratios of the appropriate elements in this residue.

A manufacturing process to allow unique tagging of each round of ammunition is here described. Assuming that the codes to be used are constructed from one pair of isotopes of each of five elements, and that 30 unique values of the ratios of the isotope pairs are used for each of the five elements, this provides for a total of $30^5$, or 24.3 million unique codes. In an assembly line process there might be 150 automated eyedroppers divided into five batches with 30 eyedroppers in each batch. Each batch of eyedroppers contains a solvent tagged with one of the five elements to be used in constructing the codes. Each eyedropper within a given batch would contain a solvent tagged at a unique value of the 30 different values used to encode that element. As the ammunition passes through the assembly line, each round would receive a total of five drops, receiving one drop from only one eyedropper in each of the five batches of 30 eyedroppers. By using an appropriate, such as automated, control system, each round of ammunition would receive a unique combination of drops, and therefore a unique combination of isotopes. Additional individual eyedroppers could be included in the assembly line which provide additional drops containing additional tags to every round of ammunition. These additional tags could encode information used to indicate constant factors such as the name of the manufacturer, the location of the plant, and the caliber of the ammunition, among other things. This method is not limited to ammunition; a similar assembly line process could be used for many other products requiring tagging of individual production units.

EXAMPLES

The following examples illustrate the present invention as applied to different substances. These examples utilized a limited number of solutions containing controlled ratios of neodymium and dysprosium isotopes. The methods illustrated are useful with other isotopes and other elements. The primary solutions used in each of the following examples were prepared as follows:

1) From a sample of $Nd_2O_3$ powder in which the isotope $^{143}Nd$ was present at a concentration of 90.8%, 10 mg were dissolved in 2 ml of 20% HCL. This solution was identified as Nd143.

2) From a sample of $Nd_2O_3$ powder in which the isotope $^{146}Nd$ was present at a concentration of 97.5%, 10 mg were dissolved in 2 ml of 20% Hcl. This solution was identified as Nd146.

3) From a sample of $Dy_2O_3$ powder in which the isotope $^{161}Dy$ was present at a concentration of 95.7%, 10 mg were dissolved in 2.0 ml of 20% HCL. This solution was identified as Dy161.

4) From a sample of $Dy_2O_3$ powder in which the isotope $^{163}Dy$ was present at a concentration of 96.8%, 10 mg were dissolved in 2.0 ml of 20% HCL. This solution was identified as Dy163.

5) 600 µl of solution Nd143 and 400 µl of solution Nd146 were combined in a small bottle. The liquid was evaporated on a hot plate at about 75 C. The residue was dissolved in 2.0 ml ethanol. This solution had a concentration of 2.14 mg Nd per ml ethanol with the neodymium isotopic composition: $^{142}Nd$, 1.6%; $^{143}Nd$, 54.6%; $^{144}Nd$, 3.0%; $^{145}Nd$, 0.61%; $^{146}Nd$, 39.9%; $^{148}Nd$, 0.2%; $^{150}Nd$, 0.1%. The ratio between the concentrations of $^{143}Nd$ and $^{146}Nd$ was, 1.368. This solution was identified as Nd60/40.

6) 600 µl of solution Dy161 and 400 µl of solution Dy163 were combined in a small bottle. The liquid was evaporated on a hot plate at about 75 C. The residue was dissolved in 2.0 ml ethanol. This solution had a concentration of 2.18 mg Dy per ml ethanol with the dysprosium isotopic composition: $^{156}Dy$, <0.1%; $^{158}Dy$, <0.1%; $^{160}Dy$, 0.1%; $^{161}Dy$, 55.0%; $^{162}Dy$, 2.0%; $^{163}Dy$, 41.9%; $^{164}Dy$, 1.0%. The ratio between the concentrations of $^{161}Dy$ and $^{163}Dy$ was 1.313. This solution was identified as Dy60/40.

7) Finally, a solution identified as Nd50/50 was prepared by combining 200 µl of solution Nd143, 200 µl of solution Nd146, and 400 µl of distilled water. This solution had a concentration of 2.14 mg Nd per ml water, with the neodymium isotopic composition: $^{142}$Nd, 1.5%; $^{143}$Nd, 47.4%; $^{144}$Nd, 2.7%; $^{145}$Nd, 0.61%; $^{146}$Nd, 47.5%; $^{148}$Nd, 0.2%; $^{150}$Nd, 0.1%. The ratio between the concentrations of $^{143}$Nd and $^{146}$Nd was 0.998.

The last three are the tagging solutions:

Nd60/40, with a concentration ratio of 1.368 between $^{143}$Nd and $^{146}$Nd.

Nd50/50, with a concentration ratio of 0.998 between $^{143}$Nd and $^{146}$Nd.

Dy60/40, with a concentration ratio of 1.313 between $^{161}$Dy and $^{163}$Dy.

In naturally occurring neodymium, the concentration ratio between $^{143}$Nd and $^{146}$Nd is 0.709. In naturally occurring dysprosium, the concentration ratio of between $^{161}$Dy and $^{163}$Dy is 0.759. In both the Nd60/40 and the Nd50/50 solutions, the isotope $^{145}$Nd was present at a concentration of 0.61%, which differs from its natural concentration of 8.30%, and allows the isotope $^{145}$Nd to be used as an indicator of background contamination. These solutions were applied as taggants in the following examples:

Example One (Bullets)

50 µl each of solutions Nd60/40 and Dy60/40 were applied by dropper to the hollow base of a standard 0.38 caliber unjacketed lead bullet. The bullet was placed on a hot plate at 75 C. to evaporate the liquid. A second bullet was similarly prepared by applying 50 µl each of solutions Nd50/50 and Dy60/40 to its base and evaporating the solvents. The bullets were then loaded into separate 0.38 caliber cartridges with 180 mg powder each. The cartridges were fired from a single shot 0.357 caliber handgun at a distance of about 30 feet into a target consisting of about 8 inches of tightly stacked newspaper in a paper bag. The bullets were recovered by carefully destacking the newspapers and transferring the bullets into separately labeled plastic bags.

In the laboratory, the bullets were each washed separately in 8 ml of 20% HCL in an ultrasonic bath for 10 minutes. The bullets were removed, and rinsed with distilled water. The isotopic compositions of neodymium and dysprosium in the recovered liquids were measured using the technique of Inductively Couple Plasma Mass Spectrometry (ICPMS). For both bullets, the ratio between the concentrations of $^{161}$Dy and $^{163}$Dy was 1.309. For the bullet labeled with the Nd50/50 solution, the ratio between the concentrations of $^{143}$Nd and $^{146}$Nd was 1.372, while for the bullet labeled with the Nd60/40 solution, the ratio between the concentrations of $^{143}$Nd and $^{146}$Nd was 1.007. Repeated measurements with ICPMS indicated a standard deviation of 1% in these isotope ratio measurements. The correlation between the applied taggant and the recovered signal is smaller than the standard deviation in the measurements, indicating that the tagging signal was carried through the processes of loading and firing the ammunition, and through the processes of recovering and analyzing the spent bullet. These results also demonstrate the ability to clearly distinguish between two bullets tagged using this technique.

Example Two (Explosives)

A sample of 10.0 g of Superfine black FFFG rifle powder was placed in a 100 ml glass jar. To this was added 1.0 ml of the solution Dy60/40 and 2.0 ml ethanol. The mixture was stirred then left to dry at room temperature for several days. A simulated explosive device was then fabricated by placing this 10.0 g of tagged powder in a sealed polyethylene container. A small hole in the top of the container admitted a fuse. The device was placed at the bottom of an empty 3-pound coffee can. The fuse was lit and the can was loosely covered with a draped cloth. When the device exploded, the cloth was blown off the top of the can and partially burned. The residue of the explosion was collected and analyzed in two ways:

1.) The remaining pieces of the polyethylene container were collected in a crucible. They were melted and burned off over a low flame. The remaining residue in the crucible was heated to red heat over a high flame for several minutes to form an ash. After ashing, 0.13 g of residue remained. To this residue was added 5.0 ml 20% HCL. The mixture was heated for several minutes on a hot plate at 75 C. The liquid was transferred through a filter paper to a sample bottle. The washing was repeated once and the liquid from the second wash was combined with the first. This liquid was analyzed by ICPMS and found to contain dysprosium with a ratio between $^{161}$Dy and $^{163}$Dy of 1.319, which is within one standard deviation of the tagging value.

2.) The coffee can in which the device was set off also was coated with residue from the explosion. This residue was collected into a crucible. The crucible was then heated to red heat to ash the sample. After ashing, the sample was washed twice with 5.0 ml 20% HCL in a manner similar to that used with the case fragments. The liquid was collected and analyzed for dysprosium isotopic composition by ICPMS. The results showed a ratio between $^{161}$Dy and $^{163}$Dy of 1.315, again showing agreement within one standard deviation between the applied tag and the recovered signal. This also showed agreement within one standard deviation between the residue recovered from two different surfaces in one explosion.

Example Three (Bullet and Powder Combination)

In this example, tagged powder was produced by placing 180 mg Hercules Bullseye smokeless pistol powder in a 3 ml bottle. To this was added 100 µl of the Nd60/40 solution. The mixture was dried for several days at room temperature. A tagged bullet was prepared in a manner similar to that of Example One, except that it was tagged only with the Dy60/40 solution. No neodymium taggant was used on the bullet. The Dy tagged bullet and the Nd tagged powder were loaded together in a clean cartridge case. As in Example One, the cartridge was fired at a target, the bullet recovered, and the residue on the bullet analyzed by ICPMS. The ratio between the concentrations of $^{161}$Dy and $^{163}$Dy was 1.306, while the ratio between the concentrations of $^{143}$Nd and $^{146}$Nd was 1.366. These results again show correlation within one standard deviation between the applied tags and the recovered signal. These results also demonstrate that separate tags used to tag two different substances can be read after they are combined provided that the separate tags have no elements in common.

Example Four (Bullet with Background Combination)

A solution was prepared containing 100 mg Nd$_2$O$_3$ (with the naturally occurring Nd isotopic composition) dissolved in 20 ml 20% HCL. From this solution 200 µl were transferred to a small bottle and evaporated on a hot plate. The residue was re-dissolved in 2.0 ml ethanol. This solution had a Nd concentration of 416 µg per ml, with the Nd having the naturally occurring isotopic composition. To demonstrate the readability of the isotopic tag in the presence of a background signal, a bullet was first tagged in the manner of Example One with 50 μl of solution Nd60/40 which carries the taggant code signal, and then contaminated with 50 μl of the above solution to represent contamination with environmental neodymium. This bullet was anticipated then to have been tagged with 107 μg of taggant neodymium and contaminated with 21 μg of neodymium with natural isotopic composition. In the manner described in Example One, the bullet was loaded into a clean cartridge with clean powder, the cartridge fired, the bullet recovered, and the residue analyzed. The measured isotopic composition of neodymium in the recovered residue was: $^{142}$Nd, 6.38%; $^{143}$Nd, 46.80%; $^{144}$Nd, 6.90%; $^{145}$Nd, 2.04%; $^{146}$Nd, 35.66%; $^{148}$Nd, 1.21%; $^{150}$Nd, 1.13%.

To demonstrate the recovery of the taggant code signal in the presence of a background signal, it is assumed that the amount of contaminating neodymium is unknown. It is also assumed that the code signal is unknown, and that the quantity of neodymium carrying the code signal is unknown. The code signal is carried in the ratio of $^{143}$Nd to $^{146}$Nd. When the two neodymium taggant solutions were prepared, however, the concentration of the $^{145}$Nd isotope was held constant at 0.61%, independent of the value of the $^{143}$Nd:$^{146}$Nd ratio. In the recovered residue, the concentration of $^{145}$Nd was measured to be 2.04%. Because it is known that the natural abundance of $^{145}$Nd is 8.30%, the concentration of contaminating neodymium in the recovered residue was determined to be 18.6%. Because it is known that the natural abundances of $^{143}$Nd and $^{146}$Nd are 12.18% and 17.17%, respectively, the fraction of the residue containing the code was determined to have $^{143}$Nd and $^{146}$Nd concentrations of 54.71% and 39.88%, respectively. These are well within one standard deviation of the code value originally used to tag the bullet. Thus, it was possible to read the taggant code signal, even in the presence of a background signal.

Example Five (Paper)

A sheet of typing paper was tagged by dripping 50 μl of the Nd60/40 solution onto the center of the paper and letting it evaporate. To read the taggant signal, the area of the paper which had been wetted by the solution was cut up into small pieces and placed in a crucible. The paper was then charred and ashed over a flame. The residue was washed twice with 20% HCL as described in Example Three. The isotopic composition of Nd in the collected liquid was determined by ICPMS. The ratio between the concentrations of $^{143}$Nd and $^{146}$Nd was 1.360. This again corresponds within one standard deviation of the composition of the applied tag.

Example Six (Epoxy)

Approximately 500 mg each of the two parts of a two part epoxy system were mixed together in an aluminum foil container. To this was added 50 μl of the Nd60/40 tagging solution. The resulting combinations was mixed thoroughly and allowed to cure. A portion of the cured epoxy was transferred to a crucible, burned, and ashed. The residue was twice washed with 20% HCL as described in Example Two. The isotopic composition of Nd in the collected liquid was determined by ICPMS. The ratio between the concentrations of $^{143}$Nd and $^{146}$Nd was 1.353. This corresponds within one standard deviation to the composition of the applied tag.

Example Seven (Paint)

One ml of an automotive touch up paint was combined with 50 μl of the Nd60/40 tagging solution. The mixture was spread over a plastic surface and allowed to dry. A portion of the dried paint was peeled from the surface, transferred to a crucible, dissolved in acetone, and the resulting mixture ignited. After combustion, the residue was ashed at red heat over a flame. The residue was twice washed with 20% HCL as described in Example Two. The isotopic composition of Nd in the collected liquid was determined by ICPMS. The ratio between the concentrations of $^{143}$Nd and $^{146}$Nd was 1.353. This corresponds within one standard deviation to the composition of the applied tag.

Example Eight (Hazardous Waste)

Used motor oil was selected as a typical hazardous waste. 1.5 g of oil was transferred to a small bottle. To this was added 50 μl of the Nd60/40 solution. The oil was then agitated for several seconds to mix the taggant with the oil. The resulting mixture was poured into a container of sand to simulate a spill of oil or hazardous waste. The oil/sand combination formed a clump, which was transferred to a crucible. The mixture was heated over a flame, ignited to burn off the oil, and heated to red heat to ash the residue. The crucible and sand were washed twice at elevated temperature and once at room temperature as described in Example Two. The liquid was filtered, collected, and analyzed by ICPMS. The results obtained showed concentrations of $^{143}$Nd, $^{145}$Nd, and $^{146}$Nd of 45.76%, 1.74%, and 34.78% respectively. The concentration of $^{145}$Nd was higher than that of the tagging solutions, indicating an unexpected background contamination. Applying the same analytical technique used in Example Four, it was determined that the recovered neodymium contained 15% background contamination. After correcting for this contamination, the ratio $^{143}$Nd:$^{146}$Nd was determined to be 1.363, showing again agreement within one standard deviation between the applied tag and the recovered signal.

I claim:

1. A method of tagging a substance for identification comprised of:
   a.) isolating and assigning an identification code to the substance to be tagged,
   b.) adding to the substance a taggant comprised of at least two elements, each element having at least two stable isotopes in a selected artificial isotopic abundance ratio wherein said abundance ratio being unchanged by chemical reactions,
   c.) maintaining a tagging record showing the correlation between the selected isotopic abundance ratio of each element in the taggant and the assigned identification code of the substance,
   d.) measuring the isotopic abundance ratio of each element of the taggant in the substance, and
   e.) comparing the results of the measurement with the tagging record to identify the assigned identification code of the substance.

2. A method of applying taggants as described in claim 1 wherein each tagging element is added individually to the substance.

3. A method as in claim 1 wherein the tagging elements are introduced into the substance being tagged in the form of elements or compounds in solution or suspension in a liquid, to be dispersed throughout the substance.

4. A method as in claim 1 wherein one or more tagging elements are present as elements or compounds in particulate form, a number of said particles being added to the substance.

5. A method as in claim 1 wherein one or more tagging elements are present as elements or compounds embedded in a particulate matrix, a number of said particles being added to the substance.

6. The method of claim 1 wherein the substance is selected from the group comprised of: tires, paint, crude oil, fuel oil, hazardous waste, paper, ink, drugs, raw materials used in the manufacture of drugs, chemicals, compact disks, laser disks, computer disks, video tapes, audio tapes, electronic circuits, ammunition, bullets, gunpowder, explosives, currency, clothing, computers.

7. A method of tagging a substance for identification comprised of:
 a.) isolating and assigning an identification code to the substance to be tagged,
 b.) adding to the substance a taggant comprised of at least two stable isotopes of the same element having a selected artificial isotopic abundance ratio wherein said abundance ratio being unchanged by chemical reactions,
 c.) maintaining a tagging record showing the correlation between the isotopic abundance ratio in the taggant and the assigned identification code of the substance,
 d.) measuring the isotopic abundance ratio of the taggant in the substance, and
 e.) comparing the results of the measurement with the tagging record to identify the assigned identification code of the substance.

8. A method as in claim 7 wherein the tagging elements are introduced into the substance being tagged in the form of elements or compounds in solution or suspension in a liquid, to be dispersed throughout the substance.

9. A method as in claim 7 wherein the tagging element is present as an element or compound in particulate form, a number of said particles being added to the substance.

10. A method as in claim 7 wherein the tagging element is present as an element or compound embedded in a particulate matrix, a number of said particles being added to the substance.

11. The method of claim 7 wherein the substance is selected from the group comprised of: tires, paint, crude oil, fuel oil, hazardous waste, paper, ink, drugs, raw materials used in the manufacture of drugs, chemicals, laser disks, compact disks, computer disks, video tapes, audio tapes, electronic circuits, ammunition, bullets, gunpowder, explosives, currency, clothing, computers.

12. A method of tagging a substance for identification comprised of:
 a.) isolating and assigning an identification code to the substance to be tagged,
 b.) adding to the substance a taggant comprised of at least two elements which are selected from the group of elements having three or more stable isotopes, each selected element having at least two stable isotopes present in a selected artificial isotopic abundance ratio corresponding to the identification code of the substance, and, as an indicator of background contamination, at least one additional stable isotope present at a fixed artificial abundance which is constant for all taggants used within a class of tagged substances, the members of which are not easily distinguishable from one another without reference to identifying taggants wherein said abundance ratio being unchanged by chemical reactions,
 c.) maintaining a tagging record showing the correlation between the isotopic abundance of each element in the taggant and the assigned identification code of the substance, and a record of the concentration of the background indicating isotope or isotopes,
 d.) measuring the isotopic abundance ratio of each element of the taggant in the substance,
 e.) determining the level of background contamination of each of the coding elements by noting the change in concentration of the background indicating isotope or isotopes of each coding element,
 f.) correcting the observed concentration of the coding isotopes of each coding element for the observed background contamination of that element, and
 g.) comparing the results of the corrected measurement with the tagging record to identify the assigned identification code of the substance.

13. A method of applying taggants as described in claim 12 wherein each tagging element is added individually to the substance.

14. A method as in claim 12 wherein the tagging elements are introduced into the substance being tagged in the form of elements or compounds in solution or suspension in a liquid, to be dispersed throughout the substance.

15. A method as in claim 12 wherein one or more tagging elements are present as elements or compounds in particulate form, a number of said particles being added to the substance.

16. A method as in claim 12 wherein one or more tagging elements are present as elements or compounds embedded in a particulate matrix, a number of said particles being added to the substance.

17. The method of claim 12 wherein the substance is selected from the group comprised of: tires, paint, crude oil, fuel oil, hazardous waste, paper, ink, drugs, raw materials used in the manufacture of drugs, chemicals, laser disks, compact disks, computer disks, video tapes, audio tapes, electronic circuits, ammunition, bullets, gunpowder, explosives, currency, clothing, computers.

18. A method of tagging a substance for identification comprised of:
 a.) isolating and assigning an identification code to the substance to be tagged,
 b.) adding to the substance a taggant comprised of at least one element selected from the group of elements having three or more stable isotopes, each selected element having at least two stable isotopes present in a selected artificial isotopic abundance ratio corresponding to the identification code of the substance, and, as an indicator of background contamination, at least one additional stable isotope present at a fixed artificial abundance which is constant for all taggants used within a class of tagged substances, the members of which are not easily distinguishable from one another without reference to identifying taggants wherein said abundance ratio being unchanged by chemical reactions,
 c.) maintaining a tagging record showing the correlation between the isotopic abundance of each element in the taggant and the assigned identification code of the substance, and a record of the concentration of the background indicating isotope or isotopes,
 d.) measuring the isotopic abundance ratio of each element of the taggant in the substance,
 e.) determining the level of background contamination of each of the coding elements by noting the change in concentration of the background indicating isotope or isotopes of each coding element,
 f.) correcting the observed concentration of the coding isotopes of each coding element for the observed background contamination of that element, and
 g.) comparing the results of the corrected measurement with the tagging record to identify the assigned identification code of the substance.

19. A method as in claim 18 wherein the tagging elements are introduced into the substance being tagged in the form of elements or compounds in solution or suspension in a liquid, to be dispersed throughout the substance.

20. A method as in claim 18 wherein one or more tagging elements are present as elements or compounds in particulate form, a number of said particles being added to the substance.

21. A method as in claim 18 wherein one or more tagging elements are present as elements or compounds embedded in a particulate matrix, a number of said particles being added to the substance.

22. The method of claim 18 wherein the substance is selected from the group comprised of: tires, paint, crude oil, fuel oil, hazardous waste, paper, ink, drugs, raw materials used in the manufacture of drugs, chemicals, compact disks, laser disks, computer disks, video tapes, audio tapes, electronic circuits, ammunition, bullets, gunpowder, explosives, currency, clothing, computers.

23. A taggant composition comprising multiple tagging elements, each tagging element consisting of two or more stable isotopes present in a selected artificial abundance ratio corresponding to an identification code.

24. A taggant composition comprising multiple tagging elements, each tagging element consisting of two or more stable isotopes present in a selected artificial abundance ratio corresponding to an identification code and one or more isotopes present at a fixed artificial abundance independent of the identification code, such that contamination of the taggant by a naturally occurring sample of the tagging element will result in a change in isotopic composition indicative of the degree of contamination.

* * * * *